United States Patent [19]

Ecsery, deceased et al.

[11] Patent Number: 4,960,797
[45] Date of Patent: Oct. 2, 1990

[54] N-2[(4-FLUORO-PHENYL)-1-METHYL]-2-ETHYL-N-METHYL-N-PROPYNYL AMINE AND THE METHOD OF USE THEREOF

[75] Inventors: Zoltán Ecsery, deceased, late of Budapest, by Mária Escery née Jurkovich, Zoltán Jóssef Ecsery, heirs; József Knoll, Budapest; Éva Somfai, Budapest; Zoltán Török, Budapest; Éva Szinnyei, Budapest; Károly Mozsolics, Sopron, all of Hungary

[73] Assignee: Chinoin Gyogyszer es Vegyeszeti Termekek Gyara Rt., Budapest, Hungary

[21] Appl. No.: 311,436

[22] Filed: Feb. 15, 1989

Related U.S. Application Data

[63] Continuation of Ser. No. 54,117, May 26, 1987, abandoned, which is a continuation-in-part of Ser. No. 840,565, Mar. 20, 1986, abandoned.

[30] Foreign Application Priority Data

May 31, 1984 [HU] Hungary ............................. 2124/84

[51] Int. Cl.$^5$ ..................... A61K 31/135; C07C 87/28
[52] U.S. Cl. ..................... 514/654; 564/374; 564/375; 564/376; 564/377; 564/381; 564/304
[58] Field of Search ............... 564/324, 375, 376, 377, 564/381; 514/654, 656

[56] References Cited

U.S. PATENT DOCUMENTS

| | | | |
|---|---|---|---|
| 3,429,922 | 2/1969 | Beregi et al. | 564/381 |
| 3,485,874 | 12/1969 | Escery et al. | 564/381 |
| 3,496,195 | 2/1970 | Ecsery et al. | 564/381 |
| 4,105,695 | 8/1978 | Partyka et al. | 564/381 |
| 4,156,017 | 5/1979 | Krüger et al. | |
| 4,314,081 | 2/1982 | Molloy et al. | 564/347 |
| 4,835,315 | 5/1989 | Lafon | 564/345 X |

OTHER PUBLICATIONS

Wolff, "Burger Medicinal Chemistry", Part III, 4th Ed., pp. 1014–1015, (1979).
Knoll et al., "Arch. Int. Pharmacodyn.", vol. 155, pp. 154–163 (1965).
Saunders, "The Aromatic Diazo Compounds", pp. 283–284 (1945).
Goodman & Gilman. The Pharmacological Basis of Therapeutics, Fifth Edition (1975), pp. 18–183.

Primary Examiner—Robert V. Hines
Attorney, Agent, or Firm—Herbert Dubno; Jonathan Myers

[57] ABSTRACT

The invention relates to the new N-[2-/4-fluorophenyl/-1-methyl]-ethyl-N-methyl-N-propynyl amine of the Formula I

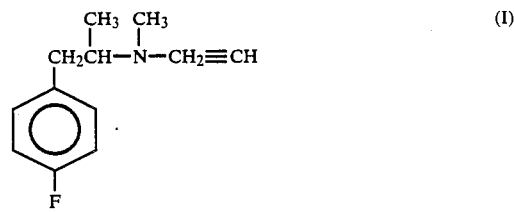

and isomers and salts thereof.

The compound of the formula I is useful as a selective MAO inhibitor.

6 Claims, No Drawings

N-2[(4-FLUORO-PHENYL)-1-METHYL]-2-ETHYL-N-METHYL-N-PROPYNYL AMINE AND THE METHOD OF USE THEREOF

This is a continuation of co-pending application Ser. No. 054,117, filed on May 26, 1987, which is a continuation-in-part of Ser. No. 840,565, filed Mar. 20, 1986, now abandoned.

The present invention is related to a new medicine and to its preparation which is acting mainly as a selective MAO-B inhibitor inhibiting the uptake of biogeneous amines and tyramine in the organism.

The present invention is directed to the biologically active compound of the formula (I)

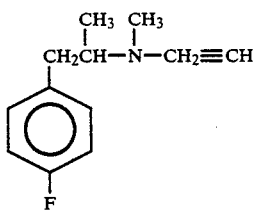
(I)

salts of this compound as well as processes serving for the preparation of the active ingredients and pharmaceutical compositions containing the active ingredient or the salts thereof.

The substituents throughout the disclosure are as defined below:

$R^1$ stands for methyl or propinyl or a radical which can be converted to methyl or propinyl, $R^2$ stands for fluorine or a radical which can be converted to fluorine, A and B when reacted with each other can form a bivalent radical of the formula

or include this radical $R^3$ stands for nitro, amino or diazonium, $R^4$ stands for hydrogen or $C_3$ saturated or unsaturated aliphatic hydrocarbon group which can be substituted by halogen, $R^5$ stands for hydrogen or methyl, X stands for halogen or a sulphonic acid ester group.

In Hungarian patent specification Nos. 154,060 and 154,655 a process for the preparation of phenylisopropylamine derivatives and their optically active derivatives is disclosed and in Hungarian patent specification No. 154,060 the coronary dilatavory, the hallucinogenic, depressant, tranquillant, analgesic and slimming activity of the compounds whereas in Hungarian patent specification No. 154,655 the monoamino oxidase (MAO) inhibitory activity of the optically active compound is disclosed.

The present invention relates to N-[2-(4-fluoro-phenyl)-1-methyl]-ethyl-N-methyl-N-propinylamine, as well as isomers and salts thereof which compounds have not been described in the literature.

The compounds of the formula (I) and the isomers and salts thereof are according to experimental data excellent MAO inhibiting substances. Their MAO-B blocking selectivity is good. They also show a long-lasting aphrodisiac activity. Their toxicity properties are also extremely good. It is very significant that next to these activities the compounds possess an activity inhibiting the uptake of biogeneous amines and tyramine.

Due to the above properties the product according to the invention is particularly suitable for the treatment of aged people. At elderly age by administration of the compound of the formula (I) the mood elements can be improved, the sexual activity can be stimulated and the motor changes can be inhibited by administrating the compound continuously, the quality of life of the elderly people can be improved. The product represents a drug which can be adopted to counteract the consequences of age-related decrease in brain dopamine concentration. It facilitates dopaminergic modulation in the brain without acting on the postsynapitc dopamine receptor, remains efficient during years of administration and is reasonably free of side-effects.

Unless otherwise emphasized that a special isomer or salt is referred to throughout the specification the product according to the invention includes all isomers and salts of the formula (I).

Our present invention is based on the recognition that in the compound group of N-alkyl-N-phenylalkylamines the position of the substituents of the phenyl ring and the quality of the substituents influence the molecule to such an extent that a generalisation could lead to errors.

Thus the special biological activity found in our invention could not be expected on the basis of the compounds which had been known from the state of the prior art and which had been explicitly disclosed.

According to a further feature of the present invention there is provided a process for the preparation of N-[2-(4-fluoro-phenyl)-1-methyl]-ethyl-N-methyl-N-propynyl-amine and isomers and salts thereof which comprises reacting a 2-phenyl-isopropyl derivative of the formula (II)

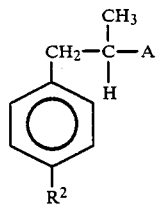
(II)

with a compound of the formula (III)

(III)

wherein $R^1$ stands for methyl or propynyl or a group which may be converted into methyl or propynyl, $R^2$ is fluorine or a group which may be converted into fluorine, A and B represent groups which on reacting with each other are capable of forming a bivalent group of the general formula

or comprise the said bivalent group and A may be attached to the carbon atom by a single or double bond—whereby in the latter case it cannot bear a hydrogen, if necessary converting in the amine of the Formula (V)

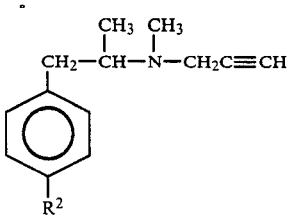

obtained the $R^2$ group into fluorine; and/or if necessary forming in the amine of the Formula (IV)

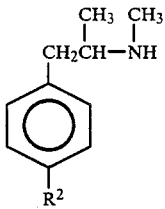

obtained the propinyl group in one or more steps; and/or subjecting a compound of the Formula (XIII)

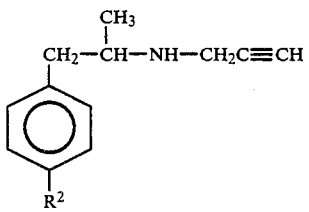

wherein $R^2$ has the same meaning as stated above—to N-methylation; whereby the three latter steps may be carried out in an optional order; and if desired converting a propinyl amine of the Formula (I) obtained into a salt formed with a mineral or organic acid or setting free the base from a salt thereof.

According to a form of realization of the process of the present invention an amine of the formula (VIII)

$$\overset{R^5}{\underset{HN-R^4}{|}} \quad (VIII)$$

wherein $R^4$ stands for hydrogen or an optionally halosubstituted, saturated or unsaturated aliphatic hydrocarbon group having 3 carbon atoms and $R^5$ is hydrogen or methyl—with a phenyl acetone derivative of the Formula (IX)

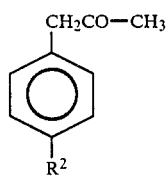

wherein $R^2$ is as stated above. In this reaction the corresponding ketimine or oxyamine is formed as intermediate which is thereafter reduced. Reduction may be carried out by methods known per se. Catalytic hydrogenation or nascent hydrogen may be used. In the compound thus obtained the $R^4$ group is converted into propinyl and/or the $R^5$ group into methyl, if necessary. The said reactions may be carried out in optional order.

According to an other form of realization of the process of the present invention an amine of the Formula (VIII) is reacted with a phenyl isopropyl derivative of the Formula (X)

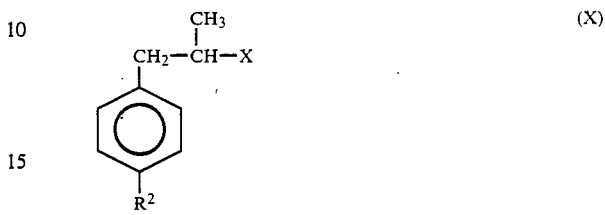

wherein $R^2$ is as stated above and X stands for halogen or a sulfonic acid ester group. X as halogen may be preferably chlorine, bromine or iodine. X as sulfonic acid ester group may be preferably an alkyl sulfonyloxy (e.g. methyl sulfonyloxy) or aryl sulfonyloxy (preferably benzene sulfonyloxy, p-toluene-sulfonyloxy or p-bromo-sulfonyloxy etc.). The reaction may be carried out advantageously in the presence of an acid binding agent. In the compound thus obtained $R^2$ may be converted into fluorine and/or $R^4$ into propinyl and/or $R^5$ into methyl, if necessary. The said reactions may be carried out in optional order.

According to a still further form of realization of the process of the present invention an amine of the formula (XI)

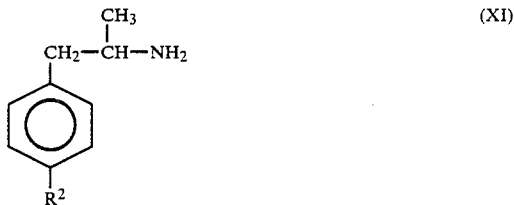

wherein $R^2$ is as stated above—is subjected to methylation and propinylation. The said reactions may be carried out in optional order.

Propinylation may be accomplished stepwise by introducing first a halopropyl or propenyl group into the molecule.

Thus one may proceed by reacting the amine of the Formula (XI) with 1,2-dibromo-propene and converting the 2-bromo-propenyl derivative thus obtained into the desired propinyl derivative by splitting off hydrogen bromide. This reaction may be carried out by reacting the 2-bromo-propenyl derivative with a base or subjecting the same to thermal treatment.

The methylation reaction according to the present invention may be carried out by reacting an amine of the formula (XIII)—wherein $R^2$ is as stated above—with formaldehyde and formic acid. One may also proceed by reacting an amine of the formula (XIII) with a methyl ester. As methylating agent a methyl halide (e.g. methyl bromide), dimethyl sulfate, methyl sulfuric acid or trimethyl phosphate may be used.

According to the another form of realization of the process of the present invention into compounds, which do not contain fluorine, a fluorine atom is introduced at any suitable stage of the synthesis. One may also proceed by using a compound of the Formula (VI)

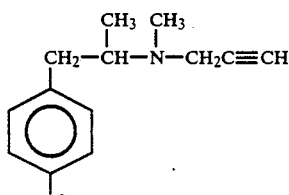

or (XII)

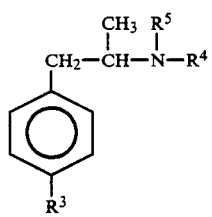

as starting material—wherein $R^3$ stands for nitro, amino or diazonium and $R^4$ and $R^5$ are as stated above. The reaction may be carried out by reducing the nitro group into an amino group, diazotizing the amino group, converting the diazonium group into diazonium-fluoroborate and forming the fluorine substituent via the latter group.

The process of the present invention encompasses the preparation of the compound of the Formula (I) in racemic and optically active form. If optically uniform antipodes are to be prepared a resolution step is to be accomplished at any suitable stage of the synthesis. Resolution may be carried out at the initial stage of the synthesis on a starting material. In this case a laevo- or dextro-rotatory starting material of the Formulae (II), (IV), (V), (VII) or (XIII)

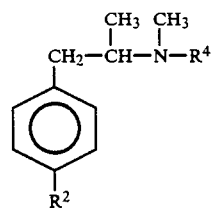

is used in the synthesis [C.A. 14 (1920) 745; Hungarian patent specification Nos. 154,635 and 169,844].

One may also proceed by subjecting a compound of the Formula (I) or (VI) to resolution. The reaction may be carried out by methods known per se by forming a diastereomer pair of salts by using a suitable optically active acid (e.g. tartaric acid or dibenzoyl tartaric acid).

The oily, lipoid soluble compounds according to the invention can be converted to water soluble salts or the free bases can be set free from the salts. Thus salts formed with hydrochloric acid, hydrogen bromide, sulphuric acid, phosphoric acid, acetic acid, formic acid, maleic acid, tartaric acid, lactic acid, 3,5-dinitrobenzoic acid, citric acid, oxalic acid can be prepared. The biologically inert or acceptable salts or the free bases are suitable for use in human medicines.

The present invention provides next to the compounds of the Formula (I) pharmaceutical compositions containing compounds of the Formula (I) and salts thereof.

The pharmaceutical compositions can be prepared by methods known per se in the form of tablets, dragees, suppositories, capsules, solutions, emulsions, injections and optionally additives, carriers, lubricating agents and filling agents can be added.

A part of the starting materials mainly the fluoro substituted derivatives has not been known from the literature and therefore the preparation of these compounds is briefly disclosed in the examples.

The pharmaceutical compositions according to the invention can be administered for adults as follows: as geriatric medicine 1-5 mg., as uptake inhibiting untidepressant 20-50 mg. and as a medicine against Parkinson's disease 5-10 mg. pro die is used.

EXAMPLE 1

8.28 g. (0.0495 mole) of ($\pm$)-N-methyl-[2-(4-fluoro-phenyl)-1-methyl]-ethyl amine (J. Am. Chem. Soc. 68 1009-1011) are dissolved in 45 ml. of toluene. To the solution 0.078 g. of benzyl triethyl ammonium chloride are added and parallelly 6.48 g. (0.0545 mole) of propargyl bromide and a solution of 2.17 g. (0.0543 mole) of sodium hydroxide in 7.5 ml. of water are added dropwise under stirring within 5 minutes. The temperature of the reaction mixture rises from 23° C. to 26° C. The reaction mixture is stirred at 26°-28° C. for 20 hours whereupon the two phases are separated, the toluene layer is dried over anhydrous sodium sulfate and evaporated. The residue is distilled at 80°-82° C./0.1 Hgmm. Thus 5.05 g. of ($\pm$)-N-methyl-N-propynyl-[2-(4-fluoro-phenyl)-1-methyl]-ethyl amine are obtained, $n_D^{20}=1.5050$. The hydrochloride melts at 132°-133° C. (from ethanol and ether).

Analysis: for the Formula $C_{13}H_{17}NClF$ Calc.: C %=65.59, H %=7.09, N %=5.79, Cl %=14.66, F %=7.85; Found: C %=65.00, H %=6.97, N %=5.95, Cl %=14.90, F %=8.01.

EXAMPLE 2

3.38 g. (0.022 mole) of ($\pm$)-N-methyl-[2-(4-fluoro-phenyl)-1-methyl]-ethyl amine are dissolved in 35 ml. of acetone, whereupon 19 g. (0.14 mole) of potassium carbonate are added and 2.95 g. (0.025 mole) of distilled propargyl bromide are added dropwise under stirring within 10 minutes. The temperature of the mixture rises from 22° C. to 25° C. The reaction mixture is heated at 55° C. for three hours and a half under stirring. The reaction mixture is allowed to stand overnight, filtered, washed three times with 25 ml. of acetone each and the acetone filtrate is evaporated. The residue is distilled at 2 Hgmm. Thus 2.28 g. of ($\pm$)-N-methyl-N-propinyl-[2-(4-fluoro-phenyl)-1-methyl]-ethyl amine are obtained, yield 51.7%. Bp.: 120°-122° C./2 Hgmm., $n_D^{20}=1.5050$.

EXAMPLE 3

30.97 g. (0.197 mole) of ($\pm$)-N-methyl-[2-(4-fluoro-phenyl)-1-methyl]-ethyl amine are dissolved in 310 ml. of acetone whereupon 174.5 g. (1.26 mole) of potassium carbonate are added and a 68% toluene solution of propargyl bromide (39.7 g., 0.227 mole) is added dropwise under stirring within 20 minutes. The temperature of the mixture rises from 26° C. to 40° C. The reaction mixture is stirred at 55° C. for six hours and a half, filtered, washed with acetone and the acetone filtrate is evaporated. The residue is distilled at 0.6 Hgmm. Thus 16.25 g. of ($\pm$)-N-methyl-N-propynyl-[2-(4-fluorophenyl)-1-methyl]-ethyl amine are obtained, yield: 41.2%. Bp.: 90°–92° C.

EXAMPLE 4

7.4 g. (0.0443 mole) of (−)-N-methyl-[2-(4-fluoro-phenyl)-1-methyl]-ethyl amine ($[\alpha]_D^{20} = -3.44°$ ethanol)) are dissolved in 60 ml. of acetone whereupon 28.9 g. (0.21 mole) of potassium carbonate are added and a 60% toluene solution of 7.56 g. (0.045 mole) of propargyl bromide is added dropwise under stirring. The reaction mixture is stirred at 35°–40° C. for 3–4 hours, filtered, washed with acetone and the acetone filtrate is evaporated. The residue is distilled at 2 Hgmm. Thus 3.3 g. of (−)-N-methyl-N-propinyl-[2-(4-fluoro-phenyl)-1-methyl]-ethyl-amine are obtained, b.p.: 120°–122° C., $n_D^{20} = 1.5052$. The hydrochloride melts at 169°–171° C. $[\alpha]_D^{20} = -6.2°$ (ethanol, c=2.4); $[\alpha]_D^{20} = -10.98°$ (water, c=2.9).

EXAMPLE 5

An aqueous solution of 10 g. (0.028 mole) of (−)-N-methyl-[2-(4-fluoro-phenyl)-1-methyl]-ethyl amine (+)-tartarate-dihydrate (mp.: 88°–91° C.) is made alkaline with a 40% aqueous sodium hydroxide solution (pH 12–13). The solution is extracted with dichloro methane and the dichloro methane extract is dried over sodium sulfate.

To the above dichloro methane solution 22.5 g. (0.16 mole) of potassium carbonate are added whereupon 60% toluene solution of 5.96 g. of propargyl bromide is added dropwise. The reaction mixture is stirred at room temperature for 5 hours, filtered and the filtrate is extracted first four times with 25 ml. of 20% acetic acid each and thereafter four times with 25 ml. of 10% hydrochloric acid each. The aqueous hydrochloric acid extracts are made alkaline with a 40% sodium hydroxide solution and extracted with dichloro methane. The dichloro methane solution is dried and gaseous hydrogen chloride is introduced. On addition of petrolether 2.38 g. of (−)-N-methyl-N-propinyl-[2-(4-fluoro-phenyl)-1-methyl]-ethyl amine hydrochloride are obtained. Mp.: 168°–170° C. $[\alpha]_D^{20} = -10.89°$ (water, c=2.5). Yield: 47.1%.

EXAMPLE 6

From 10 g. (0.028 mole) of (−)-N-methyl-[2-(4-fluoro-phenyl)-1-methyl]-ethyl amine-(+)-tartrate dihydrate the base is set free as described in Example 5 whereupon the dichloro methane solution is evaporated. The residue is dissolved in 60 ml. of acetone, 22.5 g. (0.16 mole) of potassium carbonate are added and a 60% toluene solution of 5.96 g. of propargyl bromide is added dropwise. The reaction mixture is stirred at room temperature for 3 hours, filtered and evaporated. The residue is dissolved in toluene and extracted with a 10% hydrochloric acid. The aqueous acidic extract is made alkaline with a 40% sodium hyroxide solution to pH 12–13 and extracted with toluene. The toluene solution is dried and acidified with 31% ethanolic hydrogen chloride to pH 3. The precipitated crystalline product is filtered, washed with cold acetone and dried. Thus 2.05 g. of a product are obtained which is identical with the compound prepared according to Example 5. Yield: 40.6%.

EXAMPLE 7

To 10 g. (0.028 mole) of (−)-N-methyl-[2-(4-fluoro-phenyl)-1-methyl]-ethyl amine (+)-tartrate-dihydrate according to Example 5 a solution of 7.5 g. of sodium hydroxide in 25 ml. of water and 17 ml. of toluene are added. The mixture is stirred for 30 minutes. The phases are separated and the aqueous layer is extracted three times with 6 ml. of toluene each.

The toluene solution thus obtained is added to a solution of 1.37 g. of sodium hydroxide, 0.04 g. of benzyl triethyl ammonium chloride and 5 ml. of water. To the mixture 4.1 g. of propargyl bromide are added dropwise and the reaction mixture is stirred at room temperature for 15 hours. The phases are separated, the toluene layer is extracted twice with 7 ml. of 5% acetic acid each and twice with 10 ml. of 10% hydrochloric acid each. The aqueous-acidic extract is made alkaline by adding a 40% sodium hydroxide solution and is thereafter extracted with toluene. After drying the toluene solution is acidified to pH 3 with 31% ethanolic hydrogen chloride. The crystalline product is filtered, washed with cold acetone and dried. Thus 2.72 g. of a product are obtained which is identical with the compound prepared according to Example 5.

EXAMPLE 8

From 10 g. (0.028 mole) of (−)-N-methyl-[2-(4-fluoro-phenyl)-1-methyl]-ethyl amine (+)-tartrate dihydrate the base is set free as described in Example 7. To the dried toluene solution 24.7 g. (0.17 mole) of potassium carbonate are added whereupon a 60% toluene solution of 3.66 g. (0.03 mole) of propargyl bromide is added dropwise. The reaction mixture is stirred at room temperature and filtered. The toluene filtrate is extracted twice with 7 ml. of 5% acetic acid each and twice with 10 ml. of 10% hydrochloric acid each. The aqueous acidic extract is worked up according to Example 7. Thus 2.6 g. of a product are obtained which is identical with the compound prepared according to Example 5.

EXAMPLE 9

To a solution of 8.3 g. (0.05 mole) of (±)-N-methyl-[2-(4-fluoro-phenyl)-1-methyl]-ethyl amine, 5.4 g. (0.1 mole) of propargyl aldehyde and 100 ml. of 96% ethanol 3 g. of aluminium foils act activated with mercury chloride are added in portions at 20°–30° C. The reaction mixture is stirred at room temperature for 24 hours, filtered and the filtrate is evaporated. The residue is dissolved in a 10% hydrochloric acid, extracted with benzene, made alkaline with a 40% sodium hydroxide solution and extracted again with benzene. The benzene solution is dried and evaporated. The residue is distilled off in vacuo at 2 Hgmm. Thus 5.6 of (±)-N-methyl-N-propinyl-[2-(4-fluoro-phenyl)-1-methyl]-ethyl amine are obtained. Bp.: 120°–123° C./2 Hgmm., $n_D^{20} = 1.5055$. The melting point of the hydrochloride salt is 130°–132° C.

EXAMPLE 10

10 g. (0.065 mole) of 4-fluoro-phenyl acetone and 5.3 g. (0.097 mole) of propargyl amine are dissolved in 55 ml. of 96% alcohol. The solution is stirred for half an hour at 60° C. whereupon 1.75 g. of aluminium foils activated with mercuri chloride are added. The reaction mixture is allowed to stand overnight, whereupon 15 ml. of a 40% sodium hydroxide solution are added, the alcohol is distilled off and the residue is extracted with benzene. The benzene solution is extracted with 10% hydrochloric acid, the aqueous acidic phase is made alkaline and extracted with benzene. After drying the benzene phase is evaporated and the residue is distilled in vacuo. Thus 4.9 g. of (±)-N-propynyl-[2-(4-fluoro-phenyl)-1-methyl]-ethyl amine are obtained, yield 36%. Bp.: 134°–140° C./17 Hgmm., $n_D^{20} = 1.5031$.

4 g. of the above compound are dissolved in 25 ml. of acetone whereupon 4 g. of potassium carbonate and 4 g. of methyl iodide are added. The reaction mixture is refluxed for 2 hours, filtered and evaporated. The residue is dissolved in 10% hydrochloric acid, clarified, filtered, made alkaline with a 40% sodium hydroxide solution and extracted with toluene. After drying the toluene solution is acidified with ethanolic hydrogen chloride, the precipitated product is filtered and dried. Thus 3.1 g. of (±)-N-methyl-N-propinyl-[2-(4-fluoro-phenyl)-1-methyl]-ethyl amine hydrochloride are obtained, yield 131°–133° C.

EXAMPLE 11

To a solution of 6.0 g. (0.036 mole) of (±)-N-methyl-[2-(4-fluoro-phenyl)-1-methyl]-ethyl amine and 60 ml. of acetone 33.6 g. (0.24 mole) of potassium carbonate are added whereupoh 7.45 g. (0.037 mole) of 2,3-dibromo-propene are added dropwise at 25°–30° C. under stirring within 20-25 minutes. The reaction mixture is refluxed for 6 hours, filtered and evaporated. The residue is distilled in vacuo at 4–5 Hgmm. Thus 6.52 g. of (±)-N-methyl-N-(2-bromo-propenyl-3)-[2-(4-fluoro-phenyl)-1-methyl]-ethyl amine are obtained, yield 63.3%. Bp.: 142°–143° C., $n_D^{20} = 1.5234$.

2.5 g. of the above product are dissolved in 35 ml. of ethanol whereupon 5 ml. of a 50% potassium hydroxide solution are added. The reaction mixture is refluxed for 16 hours and evaporated. The residue is taken up in water and extracted with benzene. After drying the benzene solution is acidified with ethanolic hydrogen chloride. The precipitated product is filtered and dried. Thus 2.2 g. of (±)-N-methyl-N-propinyl-[2-(4-fluoro-phenyl)-1-methyl]-ethyl amine hydrochloride are obtained, mp.: 131°–133° C.

Pharmacological Tests

The following symbols are used:
IA=(±)-N-methyl-N-[(2-propinyl)-2-(4-fluoro-phenyl)-1-methyl]-ethylamine-hydrochloride
IB=(−)-N-methyl-N-[(2-propinyl)-2-(4-fluoro-phenyl)-1-methyl]-ethylamine-hydrochloride
pClP=(±)-N-methyl-N-[(2-propinyl)-2-(4-chloro-phenyl)-1-methyl]-ethylamine-hydrochloride
pBrP=(±)-N-methyl-N-[(2-propinyl)-2-(4-bromo-phenyl)-1-methyl]-ethylamine-hydrochloride

1. Monoamine-oxidase (MAO) inhibitory activity

1.1. In vitro tests

1.1.1. Measured in rat brain and liver nucleus free homogenate

Method: Biochem. Pharmacol. 1963, 12, 1417, 1978, 27, 1739.
Substrates:
MAO-B: $^{14}$C-PEA: 0.2 mM; spec.act. 0.5 μCi/ml.
MAO-A: $^{14}$C-5HT: 5.0 mM; spec.act. 0.25 μCi/ml.

|  | Organ | IB | IA | pClP | pBrP |
|---|---|---|---|---|---|
| IC$_{50}$ | brain | $4.57 \times 10^{-8}$ | $4.17 \times 10^{-8}$ | $1.48 \times 10^{-7}$ | $3.98 \times 10^{-7}$ |
| MAO-B (M) | liver | $1.98 \times 10^{-8}$ | $1.19 \times 10^{-8}$ | $1 \times 10^{-7}$ | $1.64 \times 10^{-7}$ |
| selsct. index | liver | 238.38 | 580.67 | 43.47 | 51.28 |

$$\text{select. index} = \frac{IC_{50} \text{ MAO-A}}{IC_{50} \text{ MAO-B}}$$

1.1.2. Measured on rat brain mitochondrium

Method: From the brain of male CFY rats weighting 200–250 g. mitochondria were prepared as follows: after decapitation a tissue homogenate was prepared in 0.25M sucrose. It was centrifuged at 1000 g. for 10 minutes and the supernatant was further centrifuged for 15 minutes at 9000 g. and the sediment was taken up in 0.25M sucrose.
Substrates:
MAO-A: $6 \times 10^{-4}$M 5HT
MAO-B: $2 \times 10^{-5}$M PEA
Results: IC$_{50}$ values (M) of IA compound: MAO-A: $5 \times 10^{-5}$. MAO-B: $3 \times 10^{-8}$.

1.2. In vivo tests measured in rats brain and liver nucleus free homogenizate Method: the rats were treated s.c. with different doses of the substances and 4 hours after the administration of the substance the organs were taken out and the MAO activity was measured as disclosed in 1.1.1.

|  | Organ | IB | IA | pBrP |
|---|---|---|---|---|
| ID$_{50}$ | brain | 0.104 | 0.076 | 5.61 |
| MAO-B (mg/kg) | liver | 0.772 | 0.292 | 8.85 |
| select. index | liver | 148.8 | 168.6 | 13.33 |

$$\text{select. index} = \frac{ID_{50} \text{ MAO-A}}{ID_{50} \text{ MAO-B}}$$

After a treatment lasting for 21 days (daily dose 0.25 mg./kg.$^{s.c.}$IA) the MAO-B inhibition was 92–94% expressed in the % of the control and the MAO-A inhibition was 0%.

2. Tyramine uptake inhibitory activity on arteria pulmonalis of rabits

Rabits of both sexes and weighting 2–4 kg. were used for the experiments. The animals were killed by a blow on the neck and the heart was immediately taken out and placed to an oxygenated Krebs solution. Composition of the Krebs solution (mmole/1.): NaCl 111, KCl 4.7, CaCl$_2$ 2.52, MgSO$_4$ 1.64, NaHCO$_3$ 25, KH$_2$PO$_4$ 1.2, glucose 11. The blood vessel was purified from the connective tissue and an 1.5 mm. wide spiral had been cut out from the tissue. The so obtained blood vessel segment was placed to a 5 ml. organ bath containing a Krebs solution through which a gas mixture consisting of 95% O$_2$ + 5% CO$_2$ was passed through and which had been thermostated at 37° C. The mechanical activity was registered on a semi-isometric compensograph by using 1 g. preloading.

The tyramine uptake was inhibited on the above preparation by compound 1B dependently on the dose $IC_{50}=4.5\times 10^{-5}M$.

3. Inhibition of the uptake of biogeneous amines (method: J. Pharm. Exp. Ther. (1969) 165, 78–86)

| Ligand | Concentration of the ligand (M) | Region | IA $IC_{50}$ (M) |
|---|---|---|---|
| NA | $5\times 10^{-8}$ | hypothalamus | $8\times 10^{-6}$ |
| 5HT | $1\times 10^{-7}$ | hippcampus | $6\times 10^{-4}$ |
| DA | $1\times 10^{-7}$ | striatum | $2\times 10^{-7}$ |

NA: $^3$H-noradrenaline
5HT: $^3$H-5-hydroxy-tryptamine
DA: $^3$H-dopamine

4. Activities stimulating the activity of external phenethylamine (PEA) (in vivo MAO-B)

4.1. Activity stimulating the nictitating membrane of anaesthetized cats

The nictitating membrane is contracted on administration i.v. dose dependently by PEA. The PEA contraction activity curves are dosis dependently shifted to the left upon the intravenous administration of IA compound at a dose of 0.1 or 0.25 mg./kg.

4.2. Increase of PEA induced stereotypic behavior

Method: Arzneimittel Forsch. (Drug Research) 22, 1178 (1972).

| | | Results: | |
|---|---|---|---|
| Compound | mg./kg. | Max-score | Total. score |
| Control | — | $0.5\pm 0.22$ | $1.17\pm 0.54$ |
| IA | 0.25 | $2.17\pm 0.31$ | $8.17\pm 0.87$ |
| | 0.1 | $1.67\pm 0.21$ | $5.67\pm 0.49$ |
| | 0.05 | $1.0\pm 0.37$ | $2.83\pm 1.01$ |

The 40 mg./kg. PEA activity is potentiated by the IA compound at a dosis 0.05–0.25 mg./kg. s.c. depending on the dose.

5. Central nervous system tests

5.1. Modified jumping test (MJT)

The compound IA does not inhibit the avoidance reflex of the rats at a dose of 15 mg./kg. (method: Knoll 1963).

5.2. Metabolic rate

The compound IA at a dose of 5 mg./kg. did not increase the metabolism of rats (method: Issekutz 1942).

5.3. Testing the activity upon the food intake

The tests were carried after 96 hours starvation on rats (n=10–13).

When administered the compound IA s.c. at a dose of 5 mg./kg. mainly the 1 hour food intake was significantly decreased and when using higher doses (10–15 mg./kg. s.c.) the 5 hours food intake was significantly decreased.

5.4. Effect on catalepsy

The catatonia induced by 3 mg./kg tetrabenazine was inhibited depending on the dose both by compound IA and IB.
$ED_{50}$-IA=2.6 mg./kg.
$ED_{50}$-IB=2.9 mg./kg.

6. Testing the sexual activity on male rats

On sluggish male rats compound IA proved to be a strong long-lasting stimulant. The afrodisiac activity of one single dose (0.1 mg./kg. and 0.25 mg./kg. rest) significantly increased the number of ejaculations 24 hours and 2–3 and 4 weeks resp. after the administration related to the control. (Method: Medical science 33, 179–180, 1982).

7. Toxicity

The tests were performed on CFY male and female albino rats weighing 100–120 g. The compounds were administered i.v. and animals were observed for 48 hours.

| | Pharmaceutical compositions | | | |
|---|---|---|---|---|
| | IA | IB | pClP | |
| $LD_{50}$ | 60 | 64 | 35 | mg./kg. |

EXAMPLE A

The following components are used:
10 g. (±)-N-methyl-N-propargyl-[2-(4-fluoro-phenyl)-1-methyl]ethyl-amine-hydrochloride
6 g. talcum
6 g. magnesium-stearate
20 g. polyvidone
90 g. corn starch
160 g. lactose
The components are homogenized and 1000 pieces of tablets were compressed from the mixture.

EXAMPLE B

The following components are blended:
110 g. (−)-N-methyl-N-propargyl-[2-(4-fluoro-phenyl)-1-methyl]-ethyl-amine-hydrochloride
7 g. talcum
5 g. magnesium-stearate
20 g. polyvidone
100 g. potato-starch
150 g. lactose
The components are homogenized and 1000 pieces of tablets are compressed from the mixture.

EXAMPLE 12

16.7 g of (±)-N-methyl-[2-(4-fluoro-phenyl)-1-methyl]-ethyl-amine are dissolved in 150 ml of acetone and 69,2 g of sodium-carbonate are added while stirring. On addition of 13,3 g of allyl-bromide the reaction mixture is refluxed for 8 hours, cooled and filtrated. The filtrate is evaporated and distilled in vacuo. 15,2 g of (±)-N-methyl-N-(2-propenyl)-[2-(4-fluoro-phenyl)-1-methyl]-ethylamine are obtained. The product is dissolved in 100 ml of carbone tetrachloride and 11,8 g of bromine are added dropwise. After stirring for 8 hours the solution is evaporated and the residue is dissolved in 400 ml of ethanol. 100 ml of a 50 w % aqueous sodium hydroxide solution are added and the reaction mixture is refluxed for 20 hours. On evaporation of the ethanol, water is added and the mixture is extracted with benzene. The benzene solution is extracted with 2N hydrochloric acid and on addition of a sodium hydroxide solution the extraction with benzene is repeated. The benzene extract is dried over sodium-sulphate, filtered and evaporated. On distillation in vacuo of the residue 5,6 g of (±)-N-methyl-N-(2-propinyl)-[2-(4-fluoro-phenyl)-1-methyl]-ethyl-amine are obtained.

Bp (0.6 Hgmm) 90°–93° C.

EXAMPLE 13

10 g of 4-fluoro-phenylacetone and 6,9 g of N-methyl-propargyl-amine are dissolved in 60 ml of 96% ethanol. 1,8 g aluminium sheet, [activated with mercury chloride] are added at 60° C. and the mixture is stirred for 10 hours, filtered and evaporated. The residue is dissolved in 10% hydrochloride acid and extracted with benzene. The aqueous layer is made alkaline and extracted with benzene, whereupon the benzene extract is dried and evaporated. The residue is distilled in vacuo. 5.1 g of (±)-N-methyl-N-(2-propinyl)-[2-(4-fluoro-phenyl)-1-methyl]-ethyl-amine are obtained.

Bp: (2 Hgmm)=120°–123° C.
$n_D^{20} = 1.5058$.

EXAMPLE 14

1,72 g of 1-(4-fluoro-phenyl)-2-chloro-propane [Acta Chim.Acad. Sci.Hung 79 (1973) 433] and 1,4 g of N-methyl-propargyl-amine are heated in a sealed tube for 5 hours. The reaction mixture is dissolved in 30% aqueous ethanol containing hydrochloric acid and evaporated. From the residue 0.35 g of (±)-N-methyl-N-(2-propinyl)-[2-(4-fluoro-phenyl)-1-methyl]-ethyl-amine hydrochloride are obtained.

Mp: 130°–132° C.

EXAMPLE 15

A solution of 8.2 g. (0.05 mole) of (±)-N-methyl-2-(4-amino-phenyl)-1-methyl-ethyl amine (HU-PS 154,060) in 30 ml. 56% fluoroboric acid and 3.5 g. (0.051 mole) of sodium nitrite in 25 ml. water are simultaneously dropped into 100 ml. of 56% fluoro boric acid under stirring and cooling at −5°–(−7°)C. so that a small excess of nitrite solution is maintained in the reaction mixture during the addition. The mixture is then stirred for a further 30 minutes at −5°–(−7°)C. and in small portions 2.5 g. freshly prepared copper (I) chloride is added to the solution. The mixture is stirred for 2 hours at room temperature and stirred for 80°–90° C. for 2 hours. After cooling the mixture is extracted with ether and the aqueous acid layer is alkalized with conc. ammonium hydroxide and extracted with benzene. The benzene extract is evaporated after drying and the residue is distilled at 10 mmHg. As a main cut 5.6 g. (±)-N-methyl-2-(4-fluorophenyl)-1-methyl-ethyl-amine (boiling point: 87°–90° C./10 mmHg) obtained which are reacted according to Example 2 with propargyl bromide and processed according to Example 2. 3.8 g. (±)-N-methyl-N-propynyl-2-(4-fluoro-phenyl)-1-methyl-ethyl-amine are obtained. Bp.: 120°–123° C./2 mmHg, $n_D^{20}=1.5054$.

EXAMPLE 16

To 7.65 g. (0.05 mole) of (±)-2-(4-fluoro-phenyl)-1-methyl-ethyl-amine (BE-PS 609 630) in 25 ml. of benzene 5.3 g. (0.05 mole) of distilled benzaldehyde are added and the solution is allowed to stand overnight and dried. To the dried solution 6.3 g. (0.05 mole) of dimethyl sulphate are added and the mixture is allowed to boil under reflux for 3 hours and after cooling under stirring a solution of 2 ml. conc. hydrochlorid acid in 50 ml. of water is added. After stirring for 1 hour the two layers are separated and the aqueous - acidic layer is alkalized with sodium hydroxide and extracted with benzene. The benzene solution is dried and evaporated and the residue is distilled in vacuo. The main cut (4.15 g., bp.: 87°–90° C./10 mmHg) is dissolved in 40 ml. of toluene and after adding 23.5 g. (0.17 mole) of potassium carbonate a solution of 3.65 g. (0.031 mole) propargyl bromide in 60% toluene is added dropwise to the mixture and it is stirred for 14 hours at room temperature. The mixture is then filtered and the filtrate acidified with 31% ethanol containing HCl until pH=3. The crystalline product is filtered and recrystallized from a mixture of ethanol and ether. 2.1 g. of (±)-N-methyl-N-propynyl-2-(4-fluoro-phenyl)-1-methyl-1-ethyl-amine hydrochloride are obtained, m.p.: 130°–132° C.

We claim:

1. A compound of the Formula (I)

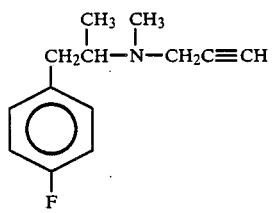

or a pharmaceutically acceptable acid addition salt thereof.

2. (±)-N-2[(4-fluoro-phenyl)-1-methyl]-2-ethyl-N-methyl-N-propynyl amine or a pharmaceutically acceptable acid addition salt thereof as defined in claim 1.

3. (−)-N-2[(4-fluoro-phenyl)-1-methyl]-2-ethyl-N-methyl-N-propynyl amine or a pharmaceutically acceptable acid addition salt thereof as defined in claim 1.

4. A pharmaceutical composition to counteract the consequences of decrease in brain dopamine concentration to facilitate dopaminergic modulation in the brain without acting on the postsynaptic dopamine receptor, and which possesses a selective B-type MAO-inhibiting activity along with a dopamine-and tyramine-uptake inhibiting activity, which comprises a therapeutically effective amount of the compound of the Formula (I)

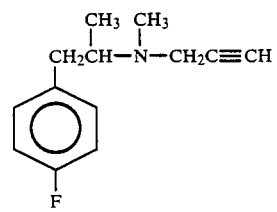

or a pharmaceutically acceptable acid addition salt thereof, in combination with a pharmaceutically acceptable inert carrier.

5. A method of treating a mammalian subject to counteract the consequences of decrease in brain dopamine concentration, to facilitate dopaminergic modulation in the brain without acting on the postsynaptic dopamine receptor by inhibiting selectively the B-type monoamine oxidase enzyme while also inhibiting tyramine and dopamine uptake, which comprises the step of administering to a mammalian subject in need of said treatment a therapeutically effective amount of the compound of the Formula (I)

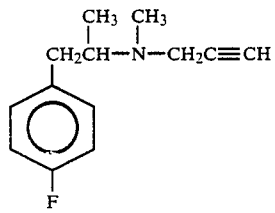

or a pharmaceutically acceptable acid addition salt thereof.

6. The method of treatment defined in claim 5 wherein the compound of the Formula (I) or the pharmaceutically acceptable acid addition salt thereof is administered to the mammalian subject in a dose of 0.05 to 0.25 mg/kg of body weight.

* * * * *